United States Patent
Heesch et al.

(10) Patent No.: US 10,456,549 B2
(45) Date of Patent: Oct. 29, 2019

(54) RESPIRATION SYSTEM AND CONNECTOR SYSTEM THEREFOR FOR REDUCING CONTAMINATIONS

(71) Applicant: Dräger Medical GmbH, Lübeck (DE)

(72) Inventors: Ralf Heesch, Lübeck (DE); Ahmet Türker, Ratekau (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 722 days.

(21) Appl. No.: 13/761,295

(22) Filed: Feb. 7, 2013

(65) Prior Publication Data

US 2013/0206145 A1    Aug. 15, 2013

(30) Foreign Application Priority Data

Feb. 10, 2012   (DE) .................. 10 2012 002 632

(51) Int. Cl.
*A61M 16/20*   (2006.01)
*A61M 16/08*   (2006.01)
(Continued)

(52) U.S. Cl.
CPC ...... *A61M 16/208* (2013.01); *A61M 16/0858* (2014.02); *A61M 16/0875* (2013.01);
(Continued)

(58) Field of Classification Search
CPC .. A61M 16/01; A61M 16/22; A61M 16/0066; A61M 16/1015; A61M 16/0833; A61M 2016/0039; A61M 2016/0042; A61M 16/1055; A61M 16/0891; A61M 16/208; A61M 16/0858; A61M 16/0875;
(Continued)

(56) References Cited

U.S. PATENT DOCUMENTS 3,835,627 A * 9/1974 Dryden ................. A61M 16/22
                                                    96/151
4,552,141 A * 11/1985 Torri .................... A61M 16/104
                                                    128/203.28
(Continued)

FOREIGN PATENT DOCUMENTS

CN         1623608 A       6/2005
CN      201668827 U      12/2010
(Continued)

*Primary Examiner* — Jan Christopher L Merene
*Assistant Examiner* — Elliot S Ruddie
(74) *Attorney, Agent, or Firm* — McGlew and Tuttle, P.C.

(57) ABSTRACT

A respiration system with a respirator (2) and with a breathing system (1), which is detachably coupled with the respirator. The coupling between the respirator and the breathing system takes place by at least two connector systems (3). The coupling between the respirator and the breathing system is designed such that the volume flow through the connector systems always takes place in only one direction. A pressure sensor (9; 9') is preferably combined with at least one of the connector systems (3) such that a unidirectional volume flow, by which the direction of migration of bacteria through the connector system is influenced in the desired manner, becomes established within this connector system (3), as a result of which the connector system and the coupled sensor are kept free from bacteria, viruses and other contaminants.

27 Claims, 3 Drawing Sheets

(51) Int. Cl.
*A61M 16/10* (2006.01)
*A61M 16/00* (2006.01)
*A61M 16/22* (2006.01)

(52) U.S. Cl.
CPC .... *A61M 16/0891* (2014.02); *A61M 16/1055* (2013.01); *A61M 16/0057* (2013.01); *A61M 16/22* (2013.01); *A61M 2016/0027* (2013.01); *A61M 2205/12* (2013.01)

(58) Field of Classification Search
CPC ...... A61M 2016/0027; A61M 2205/12; A61M 16/0057
USPC ............ 128/200.24, 202.27, 203.12–203.25, 128/204.18–204.21, 204.25, 204.26, 128/205.12, 205.24, 205.27, 205.28, 128/205.29, 207.14, 207.15, 207.16, 128/207.17, 911, 912, 909; 604/411
See application file for complete search history.

(56) References Cited

U.S. PATENT DOCUMENTS

| | | | |
|---|---|---|---|
| 5,088,486 A * | 2/1992 | Jinotti | A61M 16/0463 128/200.26 |
| 5,673,687 A * | 10/1997 | Dobson | A61M 16/16 128/200.24 |
| 5,901,705 A * | 5/1999 | Leagre | A61M 16/08 128/204.17 |
| 6,679,259 B2 | 1/2004 | Heesch | |
| 7,726,307 B2 | 6/2010 | Dittmann et al. | |
| 7,870,857 B2 * | 1/2011 | Dhuper et al. | 128/203.25 |
| 8,439,037 B2 * | 5/2013 | Winter | A61M 16/0808 128/205.24 |
| 2005/0022828 A1 | 2/2005 | Fukunaga et al. | |
| 2005/0066964 A1 | 3/2005 | Bathe | |
| 2009/0260629 A1* | 10/2009 | Yee et al. | 128/204.18 |
| 2010/0037896 A1* | 2/2010 | Mashak | 128/205.12 |
| 2011/0061650 A1 | 3/2011 | Heesch | |
| 2011/0209703 A1* | 9/2011 | Usuda et al. | 128/204.22 |
| 2012/0031402 A1* | 2/2012 | Loncar et al. | 128/203.14 |
| 2013/0000637 A1 | 1/2013 | Heesch et al. | |

FOREIGN PATENT DOCUMENTS

| | | |
|---|---|---|
| CN | 102139133 A | 8/2011 |
| DE | 10041007 C1 | 9/2001 |
| DE | 10 2005 012340 B3 | 5/2006 |
| DE | 20 2011 102764 U1 | 12/2011 |
| EP | 2 037 991 A2 | 3/2009 |
| EP | 2201979 A1 | 6/2010 |
| EP | 2298399 A1 | 3/2011 |
| EP | 2361650 A1 | 8/2011 |
| WO | 00/78380 A1 | 12/2000 |
| WO | 2007/102866 A2 | 9/2007 |

* cited by examiner

RESPIRATION SYSTEM AND CONNECTOR SYSTEM THEREFOR FOR REDUCING CONTAMINATIONS

CROSS REFERENCE TO RELATED APPLICATIONS

This application claims the benefit of priority under 35 U.S.C. § 119 of German Patent Application DE 10 2012 002 632.3 filed Feb. 9, 2012, the entire contents of which are incorporated herein by reference.

FIELD OF THE INVENTION

The present invention pertains generally to a respiration system for use in medical engineering (especially for respirating patients in the area of intensive care medicine and anesthesia). In addition, the present invention pertains to a connector system, which is used in such a respiration system. The respiration system according to the present invention comprises essentially a respirator and a breathing system, which can be detachably coupled therewith. The connector system according to the present invention is used to detachably couple the respirator with the breathing system in order to make it possible to sterilize the breathing system separately from the respirator.

BACKGROUND OF THE INVENTION

Prior-art respiration systems have, in general, a breathing circuit with an expiration branch and an inspiration branch, into which the gas components necessary for respirating the patient are introduced by means of a metered supply of fresh gas. If such a respiration system is used in the area of anesthesia, the breathing gas present in the breathing circuit is additionally enriched with an anesthetic. The respiration system is also called an anesthesia system in this case. The two terms are used as synonyms in this description, because the two types of systems differ essentially only by the additional supply of the anesthetic, but they otherwise have a very similar design.

Due to the metered supply of fresh gas (with or without anesthetic), the quantity of breathing gas consumed by the patient is replenished again and, in addition, possible leaks within the respirator are compensated. It is important especially in case of anesthesia to achieve the most effective utilization possible of the fresh gas, in which the anesthetic is also contained, in order to minimize the anesthetic consumption, on the one hand, and to protect the environment, on the other hand.

A so-called rebreathing system, in which $CO_2$ is removed from the expired (expiratory) breathing gas by means of a $CO_2$ absorber and the remaining breathing gas can again be added to the inspiratory breathing gas, is preferably used in the respiration system according to the present invention. Such a breathing system can be operated, in principle, in a half-closed mode of operation or as a largely closed breathing circuit. In the half-closed mode of operation, the quantity of fresh gas added to the breathing circuit exceeds the quantity that is taken up by a patient. The excess breathing gas is released from the breathing circuit into an anesthetic gas scavenging system during the patient's expiration phase. In the mode of operation of the closed breathing system, the breathing gases are essentially reprocessed by the $CO_2$ absorber. A suitable absorbent, for example, soda lime, is used for this. The mode of operation with closed breathing circuit is preferably used in anesthesia systems.

As was explained above, the breathing circuit of prior-art respiration systems comprises an expiratory breathing gas channel (expiration branch for short) and an inspiratory breathing gas channel (inspiration branch for short) for providing breathing gas for the patient. The inspiration branch and the expiration branch are connected to one another at their patient-side ends via a so-called Y-piece, which is used via a connected flexible tube to pass on breathing gas to the patient.

The breathing circuit usually has, besides, a breathing gas delivery unit (breathing drive) and a volume flow sensor in the inspiration branch, the breathing gas delivery unit being controlled on the basis of the output signals of the volume flow sensor. A volume of breathing gas is displaced into the patient in such respiration systems during the phase of inspiration and a volume of breathing gas expired by the patient is displaced back again into the breathing circuit of the respiration system during the phase of expiration. However, the displacement of the breathing gas volume during the phase of expiration is not usually supported, so that the expiratory resistances present in the respiration system must be overcome by the patient himself during the expiration by the patient. These expiratory resistances lead to an unintended prolongation of the duration of the phase of expiration (compared to an unhindered expiration of the breathing gas volume by the patient) and to excessive fresh gas consumption when the breathing gas is partially drawn off through the breathing gas or gaseous anesthetic escape line to reduce the expiratory resistances, as a result of which higher costs are caused and the environment is needlessly polluted by removed mixtures of gaseous anesthetics especially in the area of anesthesia because of the increased anesthetic consumption.

EP 2 201 979 A1 discloses a respiration system with a breathing circuit and with a respirator connected with the breathing circuit. The gas flow through the respirator and through the breathing system can be controlled by means of valves. U.S. Pat. No. 7,870,857 generally describes a respiration system and especially different embodiments of a breathing system, which is provided between the respirator and the mouthpiece of the patient and comprises an air humidifier.

DE 100 41 007 C1 pertains to a process for controlling a respirator, by means of which improved utilization of the fresh gas and reduction of the expiratory resistances in the breathing circuit of the respirator are achieved by a maximum percentage of the breathing gas expired by the patient being returned to the patient via a breathing gas delivery unit and at the same time only a minimum percentage of the expired breathing gas being removed unused into the environment via a gaseous anesthetic drain line. At the same time, the minimum end-expiratory pressure (PEEP—Positive End Expiratory Pressure) can be kept as low as possible. According to DE 100 41 007 C1, this is achieved by the breathing gas delivery unit present in the inspiration branch being driven down in this case at a rate that is obtained from the sum of the volume flow expired by the patient and the fresh gas volume flow supplied. A maximum percentage of the breathing gas volume expired via the expiration branch reaches in this manner at first the breathing gas delivery unit and is displaced back to the patient through the inspiration branch during the subsequent phase of inspiration.

The breathing system, which is preferably designed as a rebreathing system, of the above-described respiration system can be detachably coupled with the housing of the respirator. The breathing system, or the essential components of the breathing system are contained in a separate breathing system housing, which can be coupled with the housing of the respirator. The breathing system housing can be placed, for example, on the housing of the respirator or inserted or pushed into this housing from the top or from the side.

The components of the breathing system may comprise essentially the components of the rebreathing system (or non-rebreathing system), a $CO_2$ absorber, means for humidifying and heating the breathing air, various valves and pneumatic sensors as well as the corresponding connection pipes and connection tubes. In addition, the breathing system housing is provided with ports for the inspiration branch and the expiration branch of the patient tube system, which lead to the patient and are connected via the Y-piece described with a breathing mask for the patient to be respirated. In addition, a plurality of pneumatic ports are provided on the breathing system housing for connection to the housing of the respirator or anesthesia apparatus.

The housing of the respirator or anesthesia apparatus preferably contains a means for feeding fresh gas, means for feeding the anesthetic, a breathing gas delivery means, various pressure and volume sensors, a plurality of non-return valves, as well as all essential electrical and electronic components. Furthermore, the respirator is equipped to be connected to various means for controlling and monitoring respiration.

The purpose of the possibility of making a separation in space and in terms of function between the breathing system and the respirator is that the breathing system can be cleaned and sterilized separately from the respirator, which is important because the respirator cannot be sterilized due to the electrical and electronic components contained therein. If the respirator were exposed to the high temperatures of the sterilization process, undesired aging or failure of these components would inevitably occur.

It is apparent that the breathing system described has pneumatic and non-pneumatic connection to the respirator (therapy device). These connections are formed by so-called connectors, which usually have a "male" connector element and a "female" connector element. The combination of a male connector element and a female connector element is hereinafter also called connector system. One of the connector elements is provided on the housing of the system, while the respective corresponding connector element is provided at a corresponding location on the housing of the respirator. The connector systems and the elements thereof may be embodied by plugs, sockets, etc. When the breathing system is coupled with the respirator, the male and female connector elements that belong together mesh with one another, as a result of which at least two pneumatic connections are formed between the respirator and the breathing system.

It is apparent, furthermore, that after the breathing system is uncoupled or removed from the respirator, one of the connector elements (preferably the male element) of the connector systems remains in the housing of the respirator, because these elements are nondetachably connected to the housing of the respirator. The connector elements of the respirator and the internal lines, tubes, pipes or sensors connected thereto cannot be sterilized, because the respirator as a whole cannot be sterilized. Consequently, if bacteria, viruses or other contaminants adhere to the connector elements (and to the lines, tubes or sensors connected thereto) of the respirator, these can spread (when the breathing system is connected to the respirator) into the cleaned and sterilized breathing system.

Furthermore, the problem that the volume flows frequently flow in both directions through the respective connectors occurs in all prior-art respiration systems. In other words, expiratory air can flow from the breathing system into the respirator and then (for example, after $CO_2$ absorption) back into the breathing system in the opposite direction through one and the same connector. Due to the oscillating motion of the volume flow through the respective connectors and through the lines connected thereto, the accumulation of bacteria, viruses and other contaminants contained in the expiratory air in the connectors as well as in the lines connected thereto is further intensified. This represents a problem especially for the respirator, because this—contrary to the breathing system—cannot be sterilized. Furthermore, the various sensors (especially the pressure sensors), which are located in the housing of the respirator, are coupled with the breathing system via separate connectors in respirators according to the prior art. This means that the measuring lines of the pressure sensors of the respirator are connected via respective connectors to the expiratory and inspiratory lines of the breathing system. If bidirectional or at least oscillating volume flows likewise take place in these lines, this may also lead to an accumulation of bacteria and viruses at least in the measuring lines and in the connectors of the respirator. These bacteria and viruses may greatly proliferate under favorable conditions (temperature and humidity of the air) and subsequently spread in the previously sterilized breathing system during the respiration of a patient. In addition, the measuring lines may be clogged by contaminants to such an extent that reliable measurements cannot be guaranteed any longer.

SUMMARY OF THE INVENTION

A basic object of the present invention is therefore to make available a respiration system and a connector system for use in a respiration system, by means of which the breathing system or anesthesia apparatus can be detachably coupled with the respirator and which is designed to prevent contamination of the breathing system by a kind of "bacteria barrier" being formed between the respirator and the breathing system. An object of the present invention is, in particular, to make available a respiration system in which the pneumatic connections (connectors) between the breathing system and the respiration system are arranged and designed such that contamination of the breathing system with bacteria, viruses and other contaminants is prevented from occurring or at least reduced. Colonization of the connector systems and the elements thereof with bacteria and/or viruses shall also be prevented from occurring as much as possible in the first place.

Advantageous and preferred variants of the respiration system and connector system according to the present invention are described below. It shall be mentioned that the respiration system according to the present invention in this description is described generally for the respiration of patients. However, the basic inventive idea underlying the respiration system or the connector system may also be used in other respiration, anesthesia or breathing systems as well.

To accomplish the above objects, the coupling between the respirator and the breathing system of the respiration system according to the present invention is designed essentially such that a unidirectional volume flow, by which the direction of migration of bacteria, viruses or other contaminants through the respective connector system is affected, flows essentially through each of the connector systems between the respirator and the breathing system, so that an accumulation of bacteria, viruses or other contaminants on the connector systems is essentially prevented from occurring. At least one of the connector systems is coupled within the respirator with a sensor, and based on the unidirectional volume flow through the respective connector system, bacteria, viruses or other contaminants are prevented from accumulating on a measuring line of the coupled sensor or on the coupled sensor itself.

Furthermore, the measuring lines of the sensors (e.g., for the pressure measurement) are preferably connected to the respective connector systems or connector elements (sockets or plugs) such that accumulation of bacteria, viruses or other contaminants is essentially also prevented on the measuring lines of the coupled sensors and on the coupled sensors themselves due to the essentially unidirectional volume flow. In other words, the sensors (mostly pressure sensors) present within the respirators are preferably not coupled with the breathing system via separate connectors, but are preferably connected or coupled directly with the corresponding connector systems for the volume flows between respirator and breathing system. This coupling between the sensors (or the measuring lines thereof) and the respective connector systems takes place within the respirator. The combination of the unidirectional volume flow with the sensors or the measuring lines thereof may, of course, also take place farther in the interior of the respirator, i.e., on a line that is connected to the respective connector system and forwards the unidirectional volume flow.

A constant or even intermittent volume flow, which is necessary for the operation of the breathing system, is preferably combined or put together with the ports for the pressure measurement (i.e., with the measuring line of a pressure sensor) within a connector element of a cylindrical pipe (i.e., the male connector element) of the respective connector system, which said connector element is usually in the form of a cylindrical pipe, such that both the volume flow and the respective pressure-measuring line are merged already in front of the breathing system (i.e., within the connected respirator). It is achieved in this manner by the unidirectional volume flow that no bacteria or viruses will collect on the measuring line or on the corresponding pressure sensor, because a measuring line to a respective pressure sensor is a "dead" (dead end) line concerning the volume flow, i.e., no volume flow flows into a measuring line. It is also conceivable that the air column in the measuring line between the breathing system and the respective sensor (e.g., pressure sensor) is oscillated to and fro or temporarily compressed by changes in pressure. As long as the unidirectional volume flow is relatively high compared to this "oscillation" effect, the direction of the bacteria within the connector system is determined by the direction of the unidirectional volume flow.

As was explained above, it is especially important, on the one hand, not to send breathing gas in one direction (e.g., towards the outside into the respirator) through the same connector and, on the other hand, not to use subsequently the same path for the opposite direction (e.g., to introduce ambient air into the breathing system). However, the cross section of the gas paths used jointly in the connector system must be dimensioned such that the pressure signal will be distorted as little as possible (or that it is compensated by calculation in case of a known volume flow).

Collection and proliferation of bacteria, viruses or other contaminants in or in the vicinity of the connector systems is effectively reduced by the unidirectional volume flow. This means, on the one hand, that no bacteria or viruses present in the breathing system can enter device-side connectors of gas inlets during the operation of the respiration system, because gas can flow via the gas inlets only into the breathing system but not back into the respirator. On the other hand, this means that bacteria or viruses, which enter the breathing system from the expired air, can enter only a connector arranged in the respirator from the breathing system via a gas outlet, but they cannot enter back into the breathing system. This causes that even though bacteria and viruses may still be present within connectors of gas outlets after a sterilization and repeated connection of the breathing system, they are effectively prevented from entering the breathing system. At the same time, there is no contamination with bacteria or viruses in connectors of gas inlets, because such a contamination is effectively prevented during the operation of the respirator. Contrary to the prior-art respiration systems with bidirectional volume flows, spreading of bacteria and viruses is therefore at least reduced greatly in the present invention. This effect is especially important concerning a reduction of the spread of bacteria and viruses from the respirator into the breathing system in order to prevent contamination of the patient to be respirated.

The present invention will now be described on the basis of exemplary embodiments with reference to the figures, which show an embodiment of the connector system according to the present invention, an embodiment of the respiration system, in which this connector system or a plurality of these connector systems are used, and an enlarged view of a preferred embodiment of the connection between a connector element and a pressure sensor. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
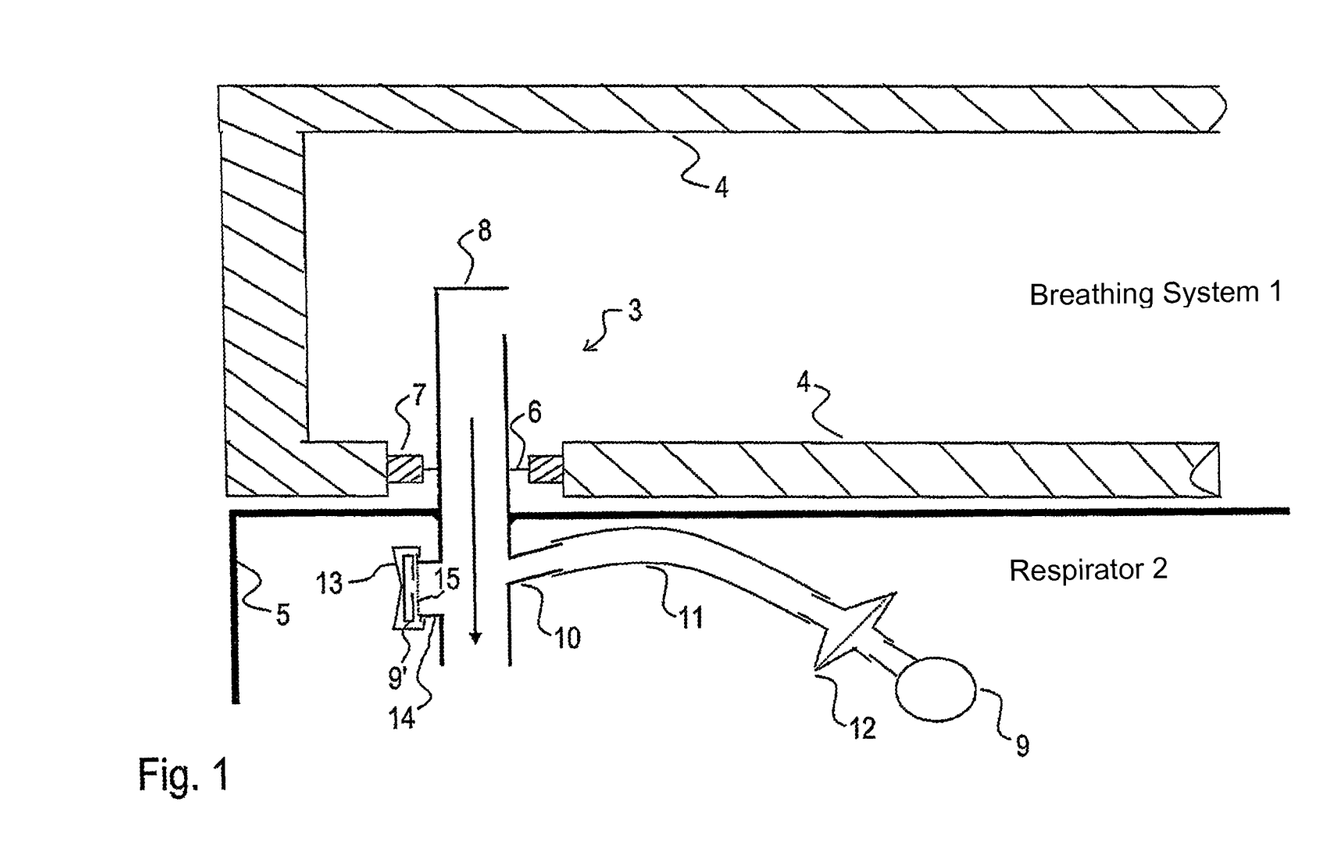
FIG. 1 is a schematic sectional view showing an exemplary embodiment of a connector system according to the present invention.

Referring to the drawings in particular, an exemplary embodiment of the connector system 3 according to the present invention will be described below with reference to FIG. 1. FIG. 1 shows a part of the housing 4 of the breathing system 1 in a cross section. As was already described above, the housing 4 of the breathing system can be placed on the housing 5 of the respirator 2 from the top or can be pushed into same, wherein the individual (male and female) connector elements of the individual connector systems 3 mesh with one another in order to bring about separable pneumatic connections between the breathing system 1 and the respirator 2.

The shown part of the breathing system housing 4 has a round passage opening 6, in which a fixed seal 7, preferably one made of an elastomer material or from another suitable material, is provided. As can be clearly recognized, a tubular socket 8 of the connector system 3 according to the present invention is inserted into the passage opening 6. Consequently, the passage opening 6 of the connector system shown forms the female connector element, while the male connector element is formed by the socket 8.

When the socket 8 of the respirator 2 is inserted into the passage opening 6 of the breathing system, the inner contact surface of the elastomer seal 7 is tightly in contact with the outer circumferential surface of the connector socket 8. It is obvious that the breathing system housing 4 can be lifted off from the connector socket 8 of the respirator 2 in an upwardly directed direction in the example being shown, and the elastomer seal 7 will then slide over the connector socket 8 of the respirator that remains in an initial position. It shall be mentioned for the sake of completeness only that at least two of the connector systems 3 shown, all of which have a similar design, are provided between the respirator 2 and the breathing system 1. Conversely, after it had been, for example, sterilized, the breathing system can again be placed on the connector socket 8 or on the connector sockets of the respirator 2 in order to again couple the breathing system with the respirator.

A continuous gas flow directed downward is provided as an example in FIG. 1 (represented by a downwardly pointing arrow, which leads from the interior of the breathing system housing 4 towards the outside into the respirator 2) within the connector socket 8. Consequently, only an outwardly directed gas flow (i.e., a gas flow from the breathing system 1 into the respirator 2) is implemented within the shown connector socket 8 of the respiration system, so that bacteria, viruses or other contaminants that may possibly be present in the connector system 3 (i.e., in the socket 8 belonging to the respirator 2 and in the lines connected thereto) are continuously forced towards the outside (i.e., back into the respirator 2). The migration of bacteria, viruses or other contaminants, which are located in the non-sterilizable respirator 2 or in the sockets 8 connected thereto (as well as in the measuring lines connected to the socket and on the sensors) into the sterilized breathing system 1 through the connector system 3 can be prevented from occurring or at least made difficult in this manner.

Figure 3:
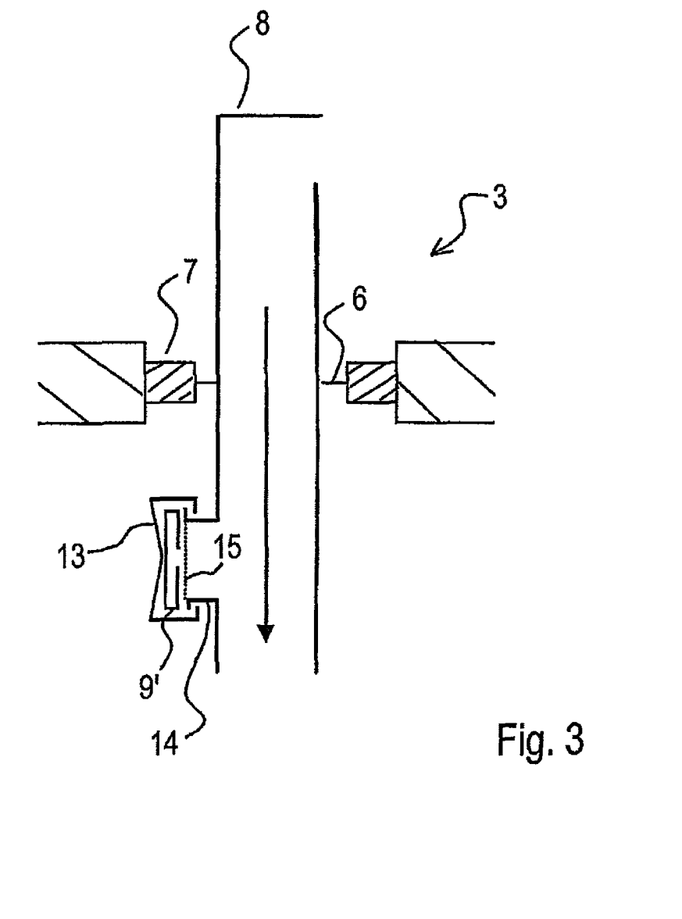
FIG. 3 is an enlarged schematic sectional view of a preferred embodiment of the connection between a connector element and a pressure sensor.

As is shown in FIG. 1, exemplary means for pressure measurement are located in the interior space of the respirator (which is not shown explicitly for reasons of better representation), for which a pressure sensor 9 or 9' is arranged at the connector socket 8 of the respirator 2 (i.e., within the respirator). Two variants (of which a preferred variant is shown in FIG. 3 in an enlarged view), which will be explained below, are shown for the arrangement of a pressure sensor in FIG. 1.

Variant 1:

A preferably slightly upwardly directed tube socket 10 for a tube 11 is arranged within the housing 5 of the respirator 2 on the side wall of the connector socket 8 of the respirator 2 (i.e., outside the breathing system housing). Due to the slight upward slope of the tube socket 10, the tube socket 10 is essentially prevented from being able to become clogged by moisture, which may possibly be present in the breathing system housing 4 or in the connector socket 8. The first end of a tube 11, which is provided with a pressure sensor 9 at its opposite, second end, is connected to the tube socket 10. As is shown in FIG. 1, a filter 12 is provided between the second tube end and the pressure sensor 9. This filter 12 may possess both water-repellant and antibacterial properties in order to protect the pressure sensor 9 against moisture, bacteria or other contaminants.

Corresponding to the change in pressure caused by the respiration process in breathing system 1 or in the breathing system housing 4, bacteria can migrate to and fro in the tube socket 10 due to cyclical compression and expansion of the gas, and they can consequently enter the connector socket 8 connected to the tube 11. Consequently, there is a risk that these bacteria can enter the housing 4 of the breathing system 1 and subsequently, via the breathing system 1, the patient's airways through the socket 8 of the connector system 3. The downwardly directed gas flow in the connector socket 8 ensures for this reason that these bacteria cannot enter the breathing system housing 4. This effect is further improved by the slight upward slope of the tube socket 10.

Variant 2:

The second variant of the connector system 3 according to the present invention is essentially a reduced embodiment of the first variant. The pressure sensor 9' is arranged in variant 2 at the end of a correspondingly shaped end section of a port socket 14 formed at the connector socket 8 of the connector system 3, for example, by means of a clamp 13. The connector socket 8 has, as can be recognized in FIG. 3, a round cross section, and the port socket 14, which likewise has an essentially round cross section with a somewhat smaller radius, is formed on a side wall of the connector socket 8 within the housing 5 of the respirator 2. The port socket is preferably sloped (angled) slightly upward, so that bacteria, viruses or other contaminants can be entrained more easily into the interior of the respirator by the downwardly directed volume flow. For protection against moisture and bacteria, a membrane 15, which may likewise possess both water-repellant and also antibacterial properties, is provided between the port socket 14 and the pressure sensor 9' (and preferably at the end of the port socket). This membrane 15 may also be extrusion-coated at the same time with a seal, which seals the pressure sensor 9' against the port socket 14 and thus also against the connector socket of the respirator 2. It is also possible to arrange the membrane 15 such that it is flush with the inner surface of the connector socket. No edges or undercuts, at which bacteria or contaminants can collect, are formed in this manner between the connector socket and the port socket.

At its outer end, the port socket is provided with a flange, which is used to mesh with the clamp 13. It is obvious that the clamp 13 can be removed from the flange with a suitable tool in order to make it possible, for example, to clear or replace the sensor 9'.

The advantage of this arrangement according to variant 2 is that the overall volume as a whole can be made considerably smaller (as a result of which the volume potentially loaded with bacteria is consequently smaller) and that the gas flow flowing in the connector socket 8 "strips off" both particles and moisture from the membrane 15 and thus maintains and secures the gas-carrying connection with the pressure sensor 9'. As was already explained, the gas flow is directed in the example being shown from the breathing system downward into the housing 5 of the respirator 2—and never in the opposite direction, i.e., the connector system is operated as a gas outlet. Consequently, even if bacteria or other contaminants should collect on the membrane 15 or in the interior of the port socket 14, these are always transported away from the breathing system by the unidirectional volume flow into the respirator, as a result of which contamination of the breathing system can be prevented but at least effectively reduced.

If a connector system 3 according to FIGS. 1 and 3 is operated with an upwardly directed gas flow, i.e., if it is used as a gas inlet, no bacteria, viruses or other contaminants can enter the breathing system, either, because no bacteria, viruses or other contaminants can collect even on a connector system 3 used as a gas inlet because of the unidirectional volume flow, because a respirator is sterile as shipped from the factory, and the unidirectional volume flow prevents or at least effectively reduces contamination from the breathing system to the respirator. Furthermore, the gases supplied and the corresponding lines are, of course, germ-free. Thus, before connecting a breathing system that was sterilized after the first operation to the respirator, it is only necessary to ensure that the connector systems are germ-free from the outside. As in prior-art respiration systems, this can already be achieved usually by wiping off with suitable detergents.

Figure 2:
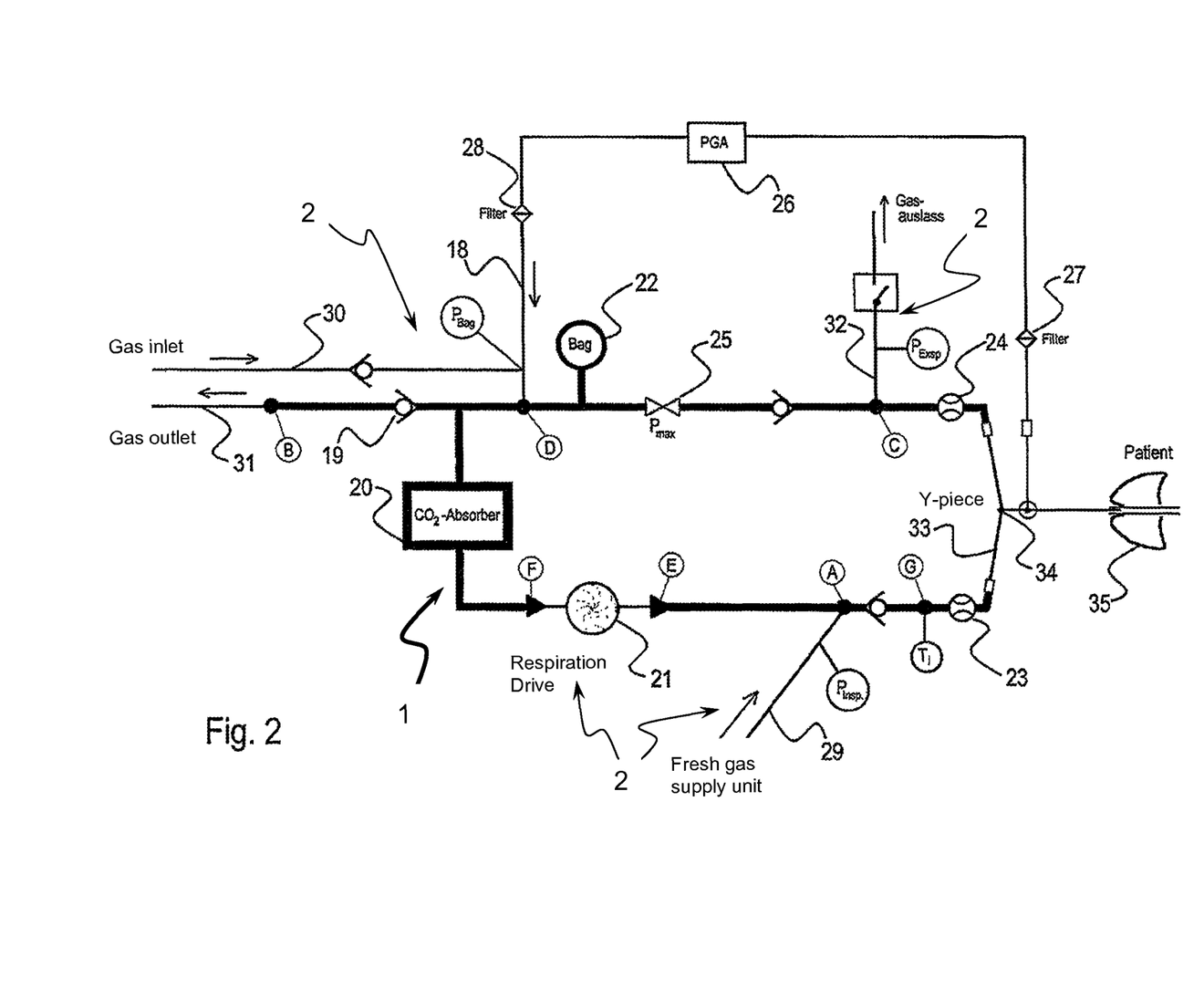
FIG. 2 is a schematic view showing an exemplary embodiment of a respiration system, in which a plurality of connector systems from FIG. 1 are used to connect the breathing system and the respirator.

FIG. 2 shows the arrangement of the different connector systems 3 from FIGS. 1 and 3 within an exemplary respiration system, which (as was explained above) comprises the respirator 2 and the breathing system 1 coupled therewith. As was explained with reference to FIG. 1, at least two connector sockets 8, which mesh with corresponding passage openings 6 in the housing 4 of the respiration system 1, are provided on the housing 5 of the respirator 2. At least two connector systems 3 must be provided, namely, a connector system for the inspiration gas and another connector system for the expiration gas.

As was described above, both the connector sockets 8 of the respirator 2 and the passage openings 6 of the breathing system 1 are connected to corresponding components of the respiration system, for example, to a $CO_2$ absorber 20, a respiration drive 21, various valves as well as to air inlets and air outlets. However, the connector systems shown in FIG. 2 are only examples. More or even alternative connector systems may also be provided between the respirator and the breathing system, namely, depending on the particular purpose and the particular embodiment of the respiration system.

The general principles of a respiration system, as they are generally shown in FIG. 2, are known to the person skilled in the art and are described in detail, among other things, in DE 100 41 007 C1 (and corresponding U.S. Pat. No. 6,679,259), which was mentioned already, as well as in EP 2 298 399 A1 (and corresponding U.S. Publication US 2011061650). U.S. Pat. No. 6,679,259 and U.S. Publication US 2011061650 are hereby incorporated by reference in their entirety.

For illustration, the lines or connections between the respective components of the breathing system or the respirator are shown in FIG. 2 in different boldnesses, the lines belonging to the breathing system being drawn bolder than the lines belonging to the respirator. It can be seen in this manner which lines or components belong to the breathing system or to the respirator. For example, the $CO_2$ absorber 20, the expiration bag (bag) 22, the volume flow sensors 23, 24, and the expiration valve 25 belong to the breathing system 1. The respiration drive 21, the gas-measuring module (PGA) 26, the filters 27, 28, the fresh gas supply unit 29 with the corresponding pressure sensor $P_{Insp}$, the gas inlet 30 with the corresponding pressure sensor $P_{Bag}$, the waste gas outlet 31, and the gas outlet 32 with the corresponding pressure sensor $P_{Exsp}$ belong to the respirator 2. It shall be mentioned that the respiration drive 21, which belongs to the respirator 2, can be separated from this and sterilized. It shall, furthermore, be noted that the patient tube system 33, to which the Y-piece 34 and the breathing mask 35 also belong, is connected to the breathing system 1 via quite normal ports (plug-type connections) close to the volume flow sensors 24, 23. The patient tube system 33 is coupled with the filter 27 of the respirator 2 via a likewise conventional plug-type connection behind the Y-piece 34.

The breathing system 1 shown in FIG. 2 is supplied with fresh gas from the respirator 2 for respirating the patient via the fresh gas supply unit 29 and through the connector system A. This influx of fresh gas takes place continuously (e.g., at 0.2 L/minute to 15 L/minute) in such a way that the volume always flows only in the direction of the breathing system 1. The additionally connected pressure sensor $P_{Insp}$ (for pressure measurement behind the respirator 21) is thus kept free from bacteria, viruses and other contaminants by the unidirectional fresh gas flow, because bacteria, viruses and other contaminants cannot leave the breathing system against the unidirectional flow and this is very extensively prevented from occurring. This was not the case with systems according to the prior art. In addition, a connector for the fresh gas supply and a separate connector for the pressure sensor $P_{Insp}$ are always provided in systems according to the prior art. Bacteria and viruses can collect in these connectors in the feed line leading to the sensor $P_{Insp}$ due to the intermittent gas flow and enter a sterilized breathing system after such a sterilized breathing system is inserted. This is prevented from occurring by the advantageous combination of connector system and measuring line or sensor in cooperation with the unidirectional volume flow.

The connector G shown is not a pneumatic connector, but it represents only a port for a temperature sensor.

Volume is released from the breathing system 1 to the outside through connector C via the gas outlet 32 (e.g., during the switch-on test, during leak tests, during rinsing operations, in case of active pressure release up to 50 L/minute). The volume flow (which is not continuous but situation-dependent) is thus always directed into the respirator 2 away from the breathing system 1. Bacteria once collected here are consequently driven continually farther towards the outside by the unidirectional volume flow. Migration of bacteria against the direction of the unidirectional volume flow is prevented or at least effectively reduced. An expiratory pressure sensor $P_{Exsp}$, which is additionally protected with a bacteria filter, as is shown in FIGS. 1 and 3, is provided at the port socket of connector C.

A volume is let through the connector system D from the outside (i.e., from the respirator 2) into the breathing system 1 (e.g., during the switch-on test, during leak tests, during rinsing operations, during active pressure release against negative pressures, etc.) via the PGA (patient gas-measuring module) 26. As is shown in FIG. 2, the PGA 26 feeds the volume flow drawn off from the Y-piece 34 via the gas supply line 18 into connector system D. The gas measurement takes place in this case according to the sidestream method instead of according to the mainstream method. This volume flow is sent through a bacteria filter 27 provided in front of the PGA 26 and through a bacteria filter 28 provided behind the PGA 26 (and in the gas supply line 18). Connector system D is rinsed by this first volume flow at a rate of approximately 200 mL/minute. It is obvious that this volume flow (which is not continuous but situation-dependent) is always directed towards the breathing system 1.

In addition, breathing gas is allowed to flow into the breathing system 1 from the respirator 2 via the gas inlet 30. This second volume flow is also always directed towards the breathing system 1. Consequently, combined volume flow, which is composed of the first volume flow in the gas supply line 18 and the second volume flow in the gas inlet line 30, is likewise also always directed towards the breathing system 1. Consequently, bacteria or other contaminants, which could spread in the breathing system 1, will not collect either in connector system D or at the sensor $P_{Bag}$, which is arranged at the connection site between the gas inlet 30 and the gas supply line 18 of the PGA 26.

Volume is let out of the breathing system 1 towards the outside into the respirator 2. If there is too much fresh gas in the system, the valve VNGF 19 arranged in front of connector system B (in the direction of flow) opens and releases the excess gas into the waste gas outlet 31. Due to the unidirectional gas flow through connector system B, bacteria and other contaminants can consequently be driven only towards the outside. It shall be noted that the pressure sensor $P_{Bag}$ may alternatively also be combined with connector system B, as is shown in FIGS. 1 and 3. The sensor $P_{Bag}$ is also kept free from any contaminants by the unidirectional volume flow through connector system B and coupling back into the breathing system is prevented from occurring or at least very extensively prevented from occurring.

Finally, the connector systems F and E are provided in order to detachably couple the respiration drive 21 with the breathing system 1. As was explained above, the respiration drive 21 (just like the breathing system 1) can be completely sterilized. Contamination with bacteria and viruses at the connector systems E, F can consequently be prevented from occurring by regular sterilization.

It shall finally be mentioned that the valves used to control the respiration system may be active and passive valves. In particular, the gas outlets are checked or controlled by passive valves (for example, simple return valves or pressure relief valves) or by actively controlled valves.

While specific embodiments of the invention have been shown and described in detail to illustrate the application of the principles of the invention, it will be understood that the invention may be embodied otherwise without departing from such principles.

APPENDIX

| | List of Reference Numbers |
|---|---|
| 1 | Breathing system |
| 2 | Respirator |
| 3 | Connector system |
| 4 | Housing of breathing system |
| 5 | Housing of respirator |
| 6 | Passage opening |
| 7 | Elastomer seal |
| 8 | Connector socket |
| 9 | Pressure sensor |
| 9' | Pressure sensor |
| 10 | Tube socket |
| 11 | Tube |
| 12 | Filter |
| 13 | Clamp |
| 14 | Port socket |
| 15 | Membrane |
| 18 | Gas supply |
| 19 | Valve VNGF |
| 20 | $CO_2$ absorber |
| 21 | Respiration drive |
| 22 | Expiration bag |
| 23 | Volume flow sensor |
| 24 | Volume flow sensor |
| 25 | Expiration valve |
| 26 | Gas-measuring module PGA |
| 27 | Filter |
| 28 | Filter |
| 29 | Fresh air supply |

-continued

| | List of Reference Numbers |
|---|---|
| 30 | Gas inlet |
| 31 | Waste gas outlet |
| 32 | Gas outlet |
| 33 | Patient tube system |
| 34 | Y-piece |
| 35 | Breathing mask |

What is claimed is:

1. A respiration system comprising:
a respirator comprising a respirator housing having a respirator housing interior space;
at least two connector systems, each of said two connector systems comprising a connector structure having a connector structure outer surface portion, a first connector structure end portion and a second connector structure end portion;
a breathing system detachably coupled with the respirator by the at least two connector systems, the breathing system comprising an expiratory branch and an inspiratory branch, said at least two connector systems being formed separate from said expiratory branch and said inspiratory branch, said breathing system comprising a breathing system housing having a breathing system housing interior space, said respirator housing and said breathing system housing defining a gap, said respirator housing having a respirator housing opening and a respirator housing outer surface, said connector structure extending from a position located in said respirator housing interior space through said respirator housing opening to another position located in said breathing system housing interior space, wherein said connector structure bridges said gap, said connector structure outer surface portion extending continuously, without interruption from said respirator housing interior space to said breathing system housing interior space, said second connector structure end portion being located in said breathing system housing interior space at a spaced location from said respirator housing outer surface, wherein said second connector structure end portion is located outside of said respirator housing outer surface, said first connector structure end portion being located in said respirator housing interior space;
a controllable gas inlet to admit gas from the respirator into the breathing system via one of the at least two connector systems;
a controllable gas outlet to draw off gas from the breathing system into the respirator via another one of the at least two connector systems;
valves controlling the controllable gas inlet and the controllable gas outlet such that only a unidirectional volume flow, by which the direction of migration of bacteria, viruses or other contaminants through the respective connector system is affected, prevails in each corresponding connector structure, so that collection of bacteria, viruses or other contaminants on the connector systems is essentially reduced, wherein gas flows only into the breathing system via the gas inlet during operation of the respirator, wherein the gas does not flow back into the respirator during operation of the respirator, wherein no bacteria or viruses present in the breathing system enters the one of the at least two connector systems associated with the gas inlet during operation of the respirator, wherein the bacteria or viruses, which enter the breathing system from expired 
fluid, enter only one of the connector systems arranged in the respirator from the breathing system via the gas outlet such that the bacteria or viruses remain in the respirator; and a sensor wherein at least one of the at least two connector systems is coupled with the sensor such that due to the unidirectional volume flow through the respective connector system, collection of bacteria, viruses or other contaminants on a measuring line of the coupled sensor or on the coupled sensor itself is essentially prevented from occurring, the measuring line being connected to the connector structure outer surface portion within the respirator housing interior space such that the measuring line is directed away from the unidirectional volume flow.

2. A respiration system in accordance with claim 1, wherein:

each of the at least one of the at least two connector systems is coupled with the sensor via a respective measuring line for the sensor, said sensor being arranged in said respirator housing interior space, said measuring line comprising an opening, wherein a filter is arranged between said opening and said sensor; and a constant or intermittent volume flow, which is necessary for the operation of the breathing system, is combined within each of the at least two connector systems with the measuring line for the corresponding sensor such that the volume flow is merged with the measuring line of the sensor or with the sensor itself already within the respirator.

3. A respiration system in accordance with claim 1, wherein the controllable gas inlet introduces gas from the respirator through one of said valves via one of the at least two connector systems into the breathing system, wherein each of the at least two connector systems is coupled with a respective sensor such that the volume flow through the connector system is a respective unidirectional flow, wherein the gas is sent in one direction through one of the connector systems and the gas is not sent in an opposite direction through the one of the connector systems, wherein the bacteria or viruses are prevented from being transferred from the respirator into the breathing system via the respective unidirectional flow from breathing system to the respirator.

4. A respiration system in accordance with claim 1, further comprising:

a further connector system; and a controllable fresh gas supply unit connected to the respirator to introduce fresh gas to the respirator and into the breathing system via the further connector system, wherein the further connector system is coupled with a respective sensor such that the volume flow through the further connector system is a further connector system unidirectional volume flow.

5. A respiration system in accordance with claim 1, further comprising another sensor, the sensor and the another sensor defining a plurality of pressure sensors, each of the pressure sensors being coupled with a corresponding one of the at least two connector systems via a respective measuring line, said measuring line comprising an arcuate portion, said measuring line comprising an opening in fluid communication with said corresponding one of the at least two connector systems and one of said pressure sensors, said one of said pressures sensors being located at a first distance from a housing of said respirator, said opening being located at a second distance from said housing of said respirator, wherein said first distance is greater than said second distance.

6. A respiration system in accordance with claim 1, wherein:

the breathing system further comprises a $CO_2$ absorber; and the $CO_2$ absorber is provided between the expiratory branch and the inspiratory branch.

7. A respiration system in accordance with claim 1, further comprising a respiration drive electrically connected to the respirator, wherein:

the breathing system comprises connectors; and the respiration drive is detachably coupled with the breathing system via the connectors.

8. A respiration system in accordance with claim 1, further comprising another sensor, the sensor and the another sensor defining a plurality of pressure sensors, each of the pressure sensors being coupled with a corresponding one of the at least two connector systems via a respective measuring line, said measuring line comprising an arcuate measuring line portion and a measuring line opening in fluid communication with said connector socket and one of said pressure sensors, wherein each connector structure comprises a connector socket essentially in the form of a cylindrical pipe that is connected with the measuring line for a corresponding pressure sensor such that the volume flow through the connector socket is merged with the respective measuring line within the respirator, each of said pressure sensors being arranged in said respirator housing interior space, said second connector structure end portion comprising a second end portion opening, said measuring line opening being located at a first distance from said second end portion opening, said one of said pressure sensors being located at a second distance from said second end portion opening, said second distance being greater than said first distance, said breathing system comprising a breathing system interior space, said second connector structure end portion being located in said breathing system interior space with said breathing system detachably connected to said respirator, said second connector structure end portion opening facing in a direction parallel to a flow of fluid in said breathing system.

9. A respiration system in accordance with claim 1, wherein each connector structure comprises:

a connector socket connected to the respirator, said first connector structure end portion being located at a spaced location from said respirator housing; and a passage opening provided in a housing of the breathing system, wherein each of the connector sockets of the respirator is inserted into a corresponding passage opening of the breathing system for coupling the breathing system with the respirator.

10. A respiration system in accordance with claim 1, wherein:

each connector structure has a connector socket connected to the respirator, said connector socket being directly connected to said respirator and said breathing system with said breathing system detachably connected to said respirator;

each connector socket has a side wall with a socket;

a pressure sensor is provided at an end of the socket, arranged within the respirator; and a filter is arranged between said pressure sensor and one of said at least two connector systems.

11. A respiration system in accordance with claim 10, further comprising pressure sensors wherein:

the socket is a tube socket;
a tube is arranged at the tube socket;
the tube forms the measuring line; and
the pressure sensors are connected to an end of the respective tubes.

12. A respiration system in accordance with claim 10, wherein the socket is sloped relative to the connector socket in a direction opposite to a direction of flow through the connector socket, whereby the socket comprises a sloped portion, said sloped portion comprising a first sloped end portion and a second sloped end portion, said first sloped end portion being located from a first distance from said respirator housing, said second sloped end portion being located at a second distance from said respirator housing, said first distance being less than said second distance.

13. A respiration system in accordance with claim 11, further comprising:
another filter to provide a plurality of filters, each of said filters being connected between the end of the tube and one of the pressure sensors.

14. A respiration system in accordance with claim 1, further comprising another sensor, the sensor and the another sensor defining a plurality of pressure sensors wherein:
each connector structure has a connector socket connected to the respirator;
a port socket is arranged on a side wall of each connector socket within the respirator; and
each pressure sensor is connected at an end of a respective port socket.

15. A respiration system in accordance with claim 14, wherein:
the port socket has an end connected with the respective pressure sensor; and
a filter membrane is provided between the end of the port socket and the pressure sensor.

16. A respiration system in accordance with claim 13, wherein:
a port socket is provided at an end with a flange;
the flange engages with a clamp; and
the respective sensor is fastened to the port socket via the clamp.

17. A respiration system in accordance with claim 15, wherein the filter membrane possesses water-repellant and/ or antibacterial properties.

18. A connector system for coupling a respirator and a breathing system, the connector system comprising:
a first connector system connecting the respirator and the breathing system to connect a controllable gas inlet of the respirator to the breathing system to admit gas from the respirator into the breathing system via the first connector system, said first connector system being formed separate from inspiration and expiration branches of the breathing system, said first connector system comprising a first connector body having a first connector body first end and a first connector body second end, said first connector body first end being located in a respirator interior space of said respirator, said first connector body second end being located in a breathing system interior space of said breathing system, wherein said first connector body bridges a gap between said respirator and said breathing system, said first connector body comprising a first connector body portion extending continuously, without interruption, from a position in said breathing system interior space to a position in said respirator interior space;
a second connector system connecting the respirator and the breathing system to connect a controllable gas outlet of the respirator to the breathing system to draw off gas from the breathing system into the respirator via the second connector system, said second connector system comprising a second connector body having a second connector body first end and a second connector body second end, said second connector body first end being located in said respirator interior space of said respirator, said connector body second end being located in said breathing system interior space of said breathing system, said second connector body comprising a second connector body portion extending continuously, without interruption, from a position in said breathing system interior space to a position in said respirator interior space, wherein said second connector body bridges another gap between said respirator and said breathing system, wherein valves control flow through the controllable gas inlet and the controllable gas outlet such that only a unidirectional volume flow, by which the direction of migration of bacteria, viruses or other contaminants through the respective connector system is affected, prevails in the first connector system and in the second connector system, so that a collection of bacteria, viruses or other contaminants on the connector systems is reduced, said second connector system being formed separate from the inspiration and expiration branches of the breathing system, wherein the gas flows only into the breathing system via the gas inlet during operation of the respirator, wherein the gas does not flow back into the respirator during operation of the respirator, wherein no bacteria or viruses present in the breathing system enters the first connector system associated with the gas inlet during operation of the respirator, wherein the bacteria or viruses, which enter the breathing system from expired fluid, enter only one of the first connector system and the second connector system arranged in the respirator from the breathing system via the gas outlet such that the bacteria or viruses remain in the respirator; and
a sensor, wherein at least one of the first connector system and the second connector system is coupled with the sensor, wherein valves control the flow through the controllable gas inlet and the controllable gas outlet such that due to the only unidirectional volume flow through the respective connector system, collection of bacteria, viruses or other contaminants on one of a measuring line of the sensor and the coupled sensor itself is essentially prevented from occurring, the measuring line being connected to one of the first connector system and the second connector system in the respirator interior space such that the measuring line extends in a direction away from the unidirectional volume flow.

19. A connector system in accordance with claim 18, wherein each of the first connector body and the second connector body comprises:
a connector socket connected to the respirator, said connector socket extending exclusively from said respirator to said breathing system with said breathing system detachably connected to said respirator; and
a socket arranged on a side wall of connector socket within the respirator, the socket having an end connected to a pressure sensor, wherein the gas is sent in a single direction in each of the first connector system and the second connector system, wherein the bacteria or viruses are prevented from being transferred from the respirator into the breathing system via a unidirectional flow of gas from the breathing system to the respirator.

20. A connector system in accordance with claim 19, wherein: the socket is a tube socket; a tube is connected to the tube socket; the tube forms the measuring line; and the pressure sensor is provided connected to an end of the tube.

21. A connector system in accordance with claim 19, wherein the socket is slightly sloped in relation to the connector socket, in a direction opposite to a unidirectional direction of flow through the connector socket, whereby the socket comprises an arcuate portion, said arcuate portion comprising a first end portion and a second end portion, said first end portion being located from a first distance from a housing of said respirator, said second end portion being located at a second distance from said housing of said respirator, said first distance being less than said second distance.

22. A connector system in accordance with claim 19, wherein a filter is provided between the tube socket and the pressure sensor.

23. A connector system in accordance with claim 18, wherein each of the first connector body and the second connector body comprises a connector socket connected to the respirator, wherein:
the connector socket has a side wall with a port socket within the respirator; and
a pressure sensor is connected to the port socket.

24. A connector system in accordance with claim 23, wherein:
a filter membrane is provided between an end of the port socket and the pressure sensor.

25. A connector system in accordance with claim 23, wherein
the port socket is provided with a flange at an end;
a clamp is provided to engage the flange to fasten the pressure sensor to the port socket.

26. A connector system in accordance with claim 24, wherein the filter membrane possesses water-repellant and/or antibacterial properties.

27. A respiration system comprising:
a respirator comprising a respirator housing, a controllable gas inlet and a controllable gas outlet, said respirator housing comprising a respirator interior space;
valves controlling the controllable gas inlet and the controllable gas outlet;
a breathing system comprising an expiratory branch and an inspiratory branch, said breathing system comprising breathing system housing having a breathing system interior space;
a first connector system connected to the respirator housing and connecting the respirator controllable gas inlet and the breathing system to admit gas from the respirator into the breathing system via the first connector system, said first connector system being formed separate from said expiratory branch and said inspiratory branch, said first connector system comprising a first connector system socket having a first connector system socket first end portion and a second connector system socket second end portion, said first connector system socket first end portion being arranged in said breathing system interior space, said second connector system socket second end portion being arranged in said respirator interior space, said first connector system socket comprising a first connector system socket outer surface portion extending continuously from said breathing system interior space to said respirator interior space;
a second connector system connected to the respirator housing and connecting the respirator controllable gas outlet and the breathing system to draw off gas from the breathing system into the respirator via the second connector system, said second connector system being formed separate from said expiratory branch and said inspiratory branch, said second connector system comprising a second connector system socket having a second connector system socket first end portion and a second connector system socket second end portion, said second connector system socket first end portion being arranged in said breathing system interior space, said second connector system socket second end portion being arranged in said respirator interior space, said second connector system socket comprising a second connector system socket outer surface portion extending continuously from said breathing system interior space to said respirator interior space, wherein said first connector system and said second connector system socket bridge a gap between said breathing system housing and said respirator housing; and
a sensor wherein at least one of the first connector system and the second connector system is coupled with the sensor, wherein:
the breathing system is detachably coupled with the respirator housing by the first connector system and the second connector system; and
the valves control flow through the controllable gas inlet and the controllable gas outlet such that only a unidirectional volume flow prevails in each of the first connector system socket and the second connector system socket by which the direction of migration of bacteria, viruses or other contaminants through the respective connector system is affected such that a collection of bacteria, viruses or other contaminants on the connector systems is reduced and the valves control flow through the controllable gas inlet and the controllable gas outlet such that due to the unidirectional volume flow through the respective connector system, collection of bacteria, viruses or other contaminants on a measuring line of the sensor or on the sensor is reduced, wherein the gas flows only into the breathing system via the gas inlet during operation of the respirator, wherein the gas does not flow back into the respirator during operation of the respirator, wherein no bacteria or viruses present in the breathing system enters the first connector system associated with the gas inlet during operation of the respirator, wherein the bacteria or viruses enter the breathing system from expired fluid, the bacteria or viruses entering only one of the first connector system and the second connector system arranged in the respirator from the breathing system via the gas outlet such that the bacteria or viruses remain in the respirator, wherein the bacteria or viruses are not transferred from the respirator into the breathing system, the measuring line being connected to one of the first connector system and the second connector system within the respirator interior space such that the measuring line extends in a direction away from the unidirectional volume flow.

* * * * *